(12) United States Patent
Kniess et al.

(10) Patent No.: US 8,906,504 B2
(45) Date of Patent: Dec. 9, 2014

(54) PIGMENTS

(75) Inventors: Helge Bettina Kniess, Roßdorf (DE); Gerhard Pfaff, Münster (DE)

(73) Assignee: Merck Patent GmbH, Darmstadt (DE)

( * ) Notice: Subject to any disclaimer, the term of this patent is extended or adjusted under 35 U.S.C. 154(b) by 1025 days.

(21) Appl. No.: 11/994,271

(22) PCT Filed: Jun. 16, 2006

(86) PCT No.: PCT/EP2006/005802
§ 371 (c)(1),
(2), (4) Date: Dec. 28, 2007

(87) PCT Pub. No.: WO2007/000253
PCT Pub. Date: Jan. 4, 2007

(65) Prior Publication Data
US 2008/0200560 A1    Aug. 21, 2008

(30) Foreign Application Priority Data
Jun. 29, 2005   (DE) .......................... 10 2005 030 242

(51) Int. Cl.
| | | |
|---|---|---|
| A61K 8/19 | (2006.01) | |
| C09C 1/00 | (2006.01) | |
| C08K 3/08 | (2006.01) | |
| B42D 15/10 | (2006.01) | |
| A23L 1/27 | (2006.01) | |
| C09D 11/00 | (2014.01) | |
| A61Q 3/02 | (2006.01) | |
| A61Q 1/02 | (2006.01) | |

(52) U.S. Cl.
CPC ......... *C09C 1/0015* (2013.01); *C09C 2200/102* (2013.01); *C09C 1/0078* (2013.01); *A61K 8/19* (2013.01); *A61K 2800/436* (2013.01); *A61Q 3/02* (2013.01); *C09C 1/0021* (2013.01); *C09C 2220/10* (2013.01); *C09C 2200/20* (2013.01); *C09C 2200/1004* (2013.01); *C09C 2200/1087* (2013.01); *C09C 2210/60* (2013.01); *A61Q 1/02* (2013.01)
USPC ............ 428/403; 428/402; 514/769; 524/435

(58) Field of Classification Search
USPC .................................................. 428/402–403
See application file for complete search history.

(56) References Cited

U.S. PATENT DOCUMENTS

| | | | | |
|---|---|---|---|---|
| 4,867,793 A | * | 9/1989 | Franz et al. .................... | 106/415 |
| 5,626,661 A | * | 5/1997 | Schmid et al. ................. | 106/415 |
| 6,063,180 A | * | 5/2000 | Korschen et al. ............. | 106/456 |
| 2002/0022093 A1 | * | 2/2002 | Kuntz et al. ..................... | 428/29 |
| 2004/0151827 A1 | | 8/2004 | Argoitia et al. | |
| 2006/0172220 A1 | * | 8/2006 | Patel et al. ............... | 430/137.14 |

FOREIGN PATENT DOCUMENTS

| | | |
|---|---|---|
| EP | 0 246 523 A2 | 11/1987 |
| EP | 0 668 329 A2 | 8/1995 |
| EP | 0 913 432 A1 | 5/1999 |

* cited by examiner

*Primary Examiner* — Ronak Patel
(74) *Attorney, Agent, or Firm* — Millen, White, Zelano & Branigan, P.C.

(57) ABSTRACT

The present invention relates to pigments comprising a substrate and, applied thereto, an iron-containing coating comprising metallic iron, process for the preparation of the pigments according to the invention, and the use thereof.

19 Claims, No Drawings

PIGMENTS

The present invention relates to pigments comprising a substrate and, applied thereto, an iron-containing coating comprising metallic iron, to a process for the preparation of the pigments according to the invention, and to the use thereof.

The use of effect pigments in a very wide variety of applications is increasing in importance. In the automobile sector, in the colouring of plastics, in cosmetics, but also in the printing sector, use is increasingly being made of effect pigments, which are intended to impart a particular lustre or particular colour effects to the products pigmented therewith. In general, the effect pigments are substrates, for example comprising metals, mica or synthetic flakes of $SiO_2$, glass or $Al_2O_3$, which are coated with one or more layers, for example comprising metals or metal oxides. In particular, metal oxides are frequently used layer materials since they can be applied to the substrates by precipitation and are substantially chemically inert. A common metal oxide employed is iron oxide.

Iron oxide-containing effect pigments are known and are described, for example, in EP 0 307 747 or EP 0 246 523. In the coating of substrates with iron(III) oxide, pigments having a red-brown mass tone are obtained. Also known are pigments having a coating of iron(II) oxide, giving either black non-lustrous pigments or lustrous coloured pigments, depending on the proportion of the oxide. Alternatively, black pigments can be obtained by coating substrates with $Fe_3O_4$, as described in EP 1 520 883. In addition to the desired dark mass tone, iron oxide-containing pigments may also have functional properties, for example be magnetisable, depending on the type of iron oxide used.

The above-mentioned pigments have the disadvantage that they exhibit either a black mass tone or high lustre, but do not have the extremely desirable combination of these properties. However, this very combination is of particular importance, in particular, in the case of automobile paints since there is major interest on the part of automobile manufacturers and customers precisely in dark-painted vehicles with high gloss. A further disadvantage in the case of the known technical solutions is that, in order to produce the desired dark hue and in order to produce hiding power, carbon black as black pigment has to be added. The absorbent and light-scattering carbon black causes losses in lustre.

In the case of the known magnetisable iron oxide-containing pigments, it is in addition disadvantageous that this magnetisability is always associated with a dark mass tone, namely dark-brown, grey or black.

There is therefore a demand for novel pigments which, with a neutral mass tone, have additional interesting optical effects and high lustre. In addition, there is a demand for functional, in particular magnetisable pigments which have a broad colour spectrum and are easily magnetisable.

The present invention accordingly relates to pigments comprising a substrate and a coating comprising metallic iron.

In a first embodiment, the pigments according to the invention have high lustre and at the same time are colour-neutral, preferably grey-black. In addition, they exhibit an interference with a noble appearance, for example silvery or gold-coloured. In addition, the coating comprising metallic iron is free from carbon or other impurities which originate from reduction using hydrocarbons or metals, such as, for example, lithium, sodium, calcium or other metals. In the applications of the pigments according to the invention, the further addition of carbon black in order to produce certain dark hues and/or in order to produce hiding power can, in addition, be omitted entirely or partly. It is thus possible to replace carbon black partly or completely with the pigment according to the invention in various dark formulations.

In a second embodiment, the pigments according to the invention are magnetisable, have a grey-black or coloured mass tone and/or exhibit coloured interference colour effects and at the same time have a high hiding power. In addition, they can also optionally have so-called colour flop effects, i.e. colour effects which change with the illumination and/or viewing angle.

The present invention likewise relates to a process for the preparation of the interference pigments according to the invention, in which a substrate which has an iron oxide-containing coating as the outermost layer and is optionally additionally coated with one or more layers is reacted in a gas mixture comprising nitrogen and hydrogen with formation of metallic iron and is optionally coated with one or more further layers.

The pigments according to the invention can be employed in a variety of applications. The present invention therefore likewise relates to the use of interference pigments in accordance with the present invention in cosmetics, surface coatings, inks, plastics, films, in security applications, for laser marking, for colouring seed, for colouring foods or in medicament coatings and for the preparation of pigment compositions and dry preparations.

The pigments according to the invention are based on substrates, preferably on flake-form substrates, where the substrate may comprise synthetic or natural mica, phyllosilicates, glass, borosilicates, $SiO_2$, $Al_2O_3$, $TiO_2$, graphite, and/or BiOCl. In particular, the substrates are flake-form mica, flake-form glass, flake-form $SiO_2$ or flake-form $Al_2O_3$.

One or more layers comprising metal oxides, metal oxide hydrates, metal suboxides, metals, metal fluorides, metal nitrides, metal oxynitrides and/or mixtures thereof may additionally be present in the pigments according to the invention between the coating comprising metallic iron and the substrate.

The metal oxide, metal oxide hydrate, metal suboxide, metal, metal fluoride, metal nitride, metal oxynitride layers or the mixtures thereof may be of low refractive index (refractive index <1.8) or high refractive index (refractive index≥1.8). Suitable metal oxides and metal oxide hydrates are all metal oxides or metal oxide hydrates to be applied as layers, such as, for example, aluminium oxide, aluminium oxide hydrate, silicon dioxide, silicon dioxide hydrate, iron oxide, tin oxide, cerium oxide, zinc oxide, zirconium oxide, chromium oxide, titanium oxide, in particular titanium dioxide, titanium oxide hydrate and mixtures thereof, such as, for example, ilmenite or pseudobrookite. Metal suboxides which can be employed are, for example, the titanium suboxides. Suitable metals are, for example, chromium, aluminium, nickel, silver, gold, titanium, copper or alloys, a suitable metal fluoride is, for example, magnesium fluoride. Metal nitrides or metal oxynitrides which can be employed are, for example, the nitrides or oxynitrides of the metals titanium, zirconium and/or tantalum. Metal oxide, metal, metal fluoride and/or metal oxide hydrate layers and very particularly preferably metal oxide and/or metal oxide hydrate layers are preferably applied to the substrates. Furthermore, multilayered structures comprising high- and low-refractive-index metal oxide, metal oxide hydrate, metal or metal fluoride layers may also be present, with high- and low-refractive-index layers preferably alternating. Pigments comprising a multilayered structure, in particular comprising alternating high- and low-refractive-index layers, can have a colour flop when viewed from different viewing angles. If the pigments according to the invention in the coating comprising metallic iron have only low or moderate proportions of metallic iron, a coloured appearance of these pigments and, with a suitable substrate and suitable layer thickness of the coating comprising metallic iron, also a colour flop when viewed from different viewing angles may also be obtained without further layers apart from the substrate and the layer comprising metallic iron having to be present.

In addition, one or more further layers comprising metal oxides, metal oxide hydrates, metal suboxides, metal fluorides, metal nitrides, metal oxynitrides and/or mixtures thereof may also be present on the layer comprising metallic iron in the pigments according to the invention. The materials already described above are used here. Particular preference is given to metal oxide and/or metal oxide hydrate layers.

If more than one further layer is located on the layer comprising metallic iron, it is in turn advantageous to design the layer structure in such a way that high- and low-refractive-index layers alternate. It is preferred here for the outermost layer to consist of one of the said high-refractive-index materials. A layer structure of this type on the layer comprising metallic iron can result in opaque pigments which have coloured interference colours. If the multilayered structures described above are employed, interesting colour interplays may additionally be observed, depending on the illumination and/or viewing angle.

Particularly suitable materials of high refractive index are, for example, $TiO_2$, $ZrO_2$, ZnO, $SnO_2$ and/or mixtures thereof. $TiO_2$ is particularly preferred. The thickness of these layers here is in each case about 3 to 300 nm and preferably 20 to 200 nm.

Particularly suitable materials of low refractive index are, for example, $SiO_2$, $SiO(OH)_2$, $Al_2O_3$, AlO(OH), $B_2O_3$, $MgF_2$ and/or mixtures thereof. $SiO_2$ is particularly preferred. The thickness of the individual layers comprising these materials is between 3 and 300 nm, they are preferably thicker than 20 nm and up to 200 nm thick.

In principle, reactions which results in the formation of new phases, for example alloys, intermetallic compounds, novel oxidic compositions, can occur at the phase interface between the coating comprising metallic iron and an additional layer.

Depending on the material of the additional layers and the layer thicknesses thereof, the pigments according to the invention can be semi-transparent or opaque. In principle, the pigments are more opaque here the higher the proportion of metallic iron in the iron-containing coating.

In addition, the pigments according to the invention may also have additional properties which are of interest for a number of applications, in particular for various security applications. Thus, given an appropriate content of metallic iron in the iron-containing coating, electrically conductive or magnetisable pigments can also be obtained. This applies, in particular, in the case of pigments having relatively high contents of metallic iron in the coating.

Electrically conductive and/or magnetisable pigments of this type are of particular interest for security features, which are preferably applied to documents of value of all types in order to prevent counterfeiting thereof.

The combination of features which are visible without aids (colour, colour flop) with hidden features (electrical conductivity, magnetisability) is a frequently desired property of pigments here since pigments can be employed particularly simply in printing inks and thus simplify the mass production of documents of value. In this way, print images can be obtained which are optically striking and difficult to copy (colour flop), but at the same time can also be analysed by machine via the magnetisable signal produced by them or a magnetisable track which itself arises from a print image which has a random pattern.

The electrical conductivity of the pigments according to the invention can also advantageously be utilised in security applications, preferably again in combination with the colour properties of the pigments.

The shape and size of the substrates employed is not crucial per se. The substrates may be irregularly shaped, spherical or in flake form. Spherical substrates consist, for example, of $SiO_2$ or glass and have a diameter of 0.2 to 10 µm, preferably 0.5 to 5 µm. The substrates are preferably in flake form. Flake-form substrates generally have a thickness of between 0.05 and 5 µm, in particular between 0.1 and 4.5 µm. Synthetically produced substrates, such as, for example, $SiO_2$ or glass, have the advantage here that they can be produced specifically in the various thicknesses for various colouristic properties. The size of the interference pigments in the length or width can be between 1 and 250 µm, it is preferably in the range from 2 to 200 µm and very particularly preferably in the range from 2 to 100 µm. The size and thickness of the substrates can be matched to the requirements of the particular applications.

The said substrates are provided with an iron-containing coating comprising metallic iron, which preferably acts as outer optically active layer. The layer thickness of the iron-containing coating is 1 to 300 nm, preferably 1 to 100 nm. The proportion of metallic iron in the iron-containing coating is 10 to 100% by weight, preferably 30 to 99% by weight and in particular 60 to 85% by weight, based on the iron-containing coating. The metallic iron in the iron-containing coating is very particularly preferably present in combination with FeO and/or $Fe_3O_4$. In addition, further simple or complex metal oxides, for example $TiO_2$, ilmenite or pseudobrookite, may also be present in the iron-containing coating.

The iron-containing coating is preferably applied directly to a flake-form substrate, in particular comprising mica, glass, $SiO_2$ or $Al_2O_3$. If, for example, an iron-containing coating having a proportion of 10 to 100% by weight of metallic iron is present on a flake-form $SiO_2$ substrate, pigments are then obtained which have various colour flops (for example red-gold or gold-green) depending on the layer thickness of the substrate and of the iron-containing coating, have a high hiding power and at the same time are electrically conductive and/or magnetisable.

In a further embodiment, the pigments according to the invention may be provided with an additional inorganic and/or organic coating. Examples of such coatings are given, for example, in EP 0 632 109, U.S. Pat. No. 5,759,255, DE 43 17 019, DE 39 29 423, DE 32 35 017, EP 0 492 223, EP 0 342 533, EP 0 268 918, EP 0 141 174, EP 0 764 191, WO 98/13426 or EP 0 465 805, the disclosure content of which is hereby incorporated by way of reference. In addition to the optical properties already mentioned, pigments comprising an organic coating, for example comprising organosilanes or organotitanates or organozirconates, additionally have increased stability to weathering influences, such as, for example, moisture and light, which is of particular interest, especially for industrial coatings and in the automobile sector. The stabilisation can be improved by inorganic components of the additional coating. In addition, it is also possible for the additional coating to be based on inorganic materials, in particular on oxides and oxide hydrates of the elements silicon, aluminium, zinc, tin, cerium and/or zirconium. Overall, the respective proportions for the additional stabilising coating should be selected so that the optical properties of the pigments according to the invention are not significantly affected.

The pigments according to the invention can be obtained by reaction of a substrate which has an iron oxide-containing coating as the outermost layer and is optionally additionally coated with one or more layers, in a reducing gas mixture comprising nitrogen and hydrogen with formation of metallic iron, and optionally further coating of the pigments obtained in this way with one or more additional layers. This facilitates the provision of the iron-containing coating comprising metallic iron, where the layer comprising metallic iron can be located directly on the substrate, between other layers or as the outermost layer on the substrate.

In general, reductions of metal oxide layers in lustre pigments are known, for example, from DE 199 53 655, DE 198 43 014, DE 198 22 046, DE 196 18 562, DE 195 11 697 or DE 195 11 696. However, the reduction processes described in the said documents differ significantly in the procedure from that in accordance with the present invention. Other reducing agents, for example ammonia, carbon, hydrocarbons or metals, are frequently employed. A significant disadvantage of the use of the said reducing agents is contamination of the layer reduced therewith, in particular with carbon, which results in undesired changes in the colour effects actually desired. Reduction using metals is also disadvantageous since an additional component, which can likewise result in undesired changes in the properties of the pigments, is introduced into the coating at the same time in this way.

In addition, reduction of the titanium dioxide present as the uppermost layer, which results in the formation of titanium suboxides having a bluish colour, occurs in all pigments from the prior art. These coloured suboxides are the principal aim of the reduction. A reduction of iron oxide-containing coatings to metallic iron is not known. It was also not to be expected that the pigments according to the invention can be obtained in this way since iron oxides, such as $Fe_3O_4$ or FeO, usually form first in the reduction.

In the process according to the invention for the preparation of the pigments described, a substrate which is coated with an iron oxide-containing coating and may optionally have one or more further layers between the substrate and the iron oxide-containing layer is reacted in a reducing gas mixture comprising nitrogen and hydrogen with formation of metallic iron. In this way, it is ensured that the coating comprising metallic iron is free from carbon. The iron oxide present in the iron oxide-containing coating is preferably iron(III) oxide. Iron(III) oxide-containing coatings can be produced in a manner known to the person skilled in the art, for example by wet-chemical methods by precipitation from corresponding iron salts in aqueous solution or a water/solvent mixture. Precipitations of this type are known, for example, from DE 2313331.

The gas mixture comprising nitrogen and hydrogen to be employed for the reaction has a hydrogen content in the range from 2.5 to 25% by vol., in particular from 4 to 10% by vol., and very particularly preferably from 5 to 8% by vol.

The reduction of the iron oxide-containing coating is carried out at temperatures of 400 to 1000° C., preferably 500 to 900° C. and particularly preferably 550 to 850° C. The calcination duration is 15-240 minutes, preferably 30-120 minutes and in particular 30-90 minutes.

The pigment obtained in this way can subsequently, if necessary, also be coated with one or more further layers, whose composition has already been described above. These layers can, like the layers optionally likewise present on the substrate below the iron oxide-containing layer, also be applied by known methods, for example by wet-chemical methods by precipitation from corresponding metal salts in aqueous solution, by deposition from organic metal compounds in a fluidised bed and by CVD or PVD methods. Methods of this type are usually employed for the coating of pigment substrates and are described, for example, in DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017.

In addition, in a process which is likewise according to the invention, an inorganic and/or organic coating may additionally be applied as the outer layer. Examples of coating methods of this type are given, inter alia, in EP 0 632 109, U.S. Pat. No. 5,759,255, DE 43 17 019, DE 39 29 423, DE 32 35 017, EP 0 492 223, EP 0 342 533, EP 0 268 918, EP 0 141 174, EP 0 764 191, WO 98/13426 or EP 0 465 805. Examples of organic coatings and the advantages associated therewith have already been described above under structure of the pigments according to the invention. The process steps of application of the organic coating can be carried out directly after the other steps of the process according to the invention. The substances applied here comprise merely a proportion by weight of 0.1 to 5% by weight, preferably 0.5 to 3% by weight, of the pigment as a whole.

The pigments according to the invention are versatile and can be employed in many areas. Accordingly, the present invention likewise relates to the use of the pigments according to the invention in cosmetics, surface coatings, inks, plastics, films, in security applications, for colouring seed, for colouring foods or in medicament coatings, for laser marking and for the preparation of pigment compositions and dry preparations.

In the case of cosmetics, the pigments according to the invention are particularly suitable for products and formulations of decorative cosmetics, such as, for example, nail varnishes, colouring powders, lipsticks or eye shadows, soaps, toothpastes, etc. The interference pigments according to the invention can of course also be combined in the formulations with cosmetic raw materials and assistants of all types. These include, inter alia, oils, fats, waxes, film formers, preservatives and assistants which generally determine the applicational properties, such as, for example, thickeners and rheological additives, such as, for example, bentonites, hectorites, silicon dioxide, Ca silicates, gelatine, high-molecular-weight carbohydrates and/or surface-active assistants, etc. The formulations comprising interference pigments according to the invention may belong to the lipophilic, hydrophilic or hydrophobic type. In the case of heterogeneous formulations having discrete aqueous and non-aqueous phases, the particles according to the invention may be present in each case only one of the two phases or alternatively distributed over both phases.

The pH values of the aqueous formulations can be between 1 and 14, preferably between 2 and 11 and particularly preferably between 5 and 8. The concentrations of the interference pigments according to the invention in the formulation are not subject to any limits. They can be—depending on the application—between 0.001 (rinse-off products, for example shower gels) and 99% (for example lustre-effect articles for particular applications). The interference pigments according to the invention may furthermore also be combined with cosmetic active compounds. Suitable active compounds are, for example, insect repellents, UV A/BC protection filters (for example OMC, B3, MBC), antiageing active compounds, vitamins and derivatives thereof (for example vitamin A, C, E, etc.), self-tanning agents (for example DHA, erythrulose, inter alia) and further cosmetic active compounds, such as, for example, bisabolol, LPO, ectoin, emblica, allantoin, bioflavonoids and derivatives thereof.

In the case of the use of the pigments in surface coatings and inks, all areas of application known to the person skilled in the art are possible, such as, for example, powder coatings, automobile paints, printing inks for gravure, offset, screen or flexographic printing, and for surface coatings in outdoor applications. The pigments according to the invention employed for printing are preferably based on flake-form substrates. The surface coatings and inks here may be, for example, radiation-curing, physically drying or chemically curing. For the preparation of printing inks or liquid surface coatings, a multiplicity of binders, for example based on acrylates, methacrylates, polyesters, polyurethanes, nitrocellulose, ethylcellulose, polyamide, polyvinyl butyrate, phenolic resins, maleic resins, starch or polyvinyl alcohol, amino resins, alkyd resins, epoxy resins, polytetrafluoroethylene, polyvinylidene fluorides, polyvinyl chloride or mixtures thereof, is suitable, in particular water-soluble types. The surface coatings can be powder coatings or water- or solvent-based coatings, where the choice of coating constituents is subject to the general knowledge of the person skilled in the art. Common polymeric binders for powder coatings are, for example, polyesters, epoxides, polyurethanes, acrylates or mixtures thereof.

In addition, the pigments according to the invention can be used in films and plastics, for example in agricultural sheeting, infrared-reflective films and sheets, gift foils, plastic containers and mouldings for all applications known to the person skilled in the art. Suitable plastics for the incorporation of the interference pigments according to the invention are all common plastics, for example thermosets or thermoplastics. The description of the possible applications and plastics which can be employed, processing methods and additives are given, for example, in RD 472005 or in R. Glausch, M. Kieser, R. Maisch, G. Pfaff, J. Weitzel, Perlglanzpigmente [Pearlescent Pigments], Curt R. Vincentz Verlag, 1996, 83 ff., the disclosure content of which is incorporated herein.

As already described above, the pigments according to the invention can particularly advantageously be employed in security applications. A security application here is taken to mean any application in which products are provided with security features which makes the authenticity of the products evident and/or is employed for protection against counterfeits, for ensuring access authorisation, etc., or the use in equipment and measuring devices for checking these properties.

The pigments according to the invention can preferably be used in security features of documents of value. Documents of value are taken to mean products such as banknotes, cheques, credit cards, shares, passports, identity documents, access authorisation identity cards, driving licences, entry tickets, revenue stamps, postage stamps, labels, seals and the like. However, the pigments according to the invention can also be employed in security features in packaging materials, such as, for example, packaging of medicaments, foods, perfumes, cigarettes and the like, or directly on products of daily use, such as, for example, clothing, shoes, household articles, domestic electronic articles and the like. Any form of a security feature which may comprise pigments is suitable here, for example labels, full- or part-area coatings, prints, holographic elements, etc. The security feature here can have a single- or multilayered structure and be present in combination with one or more other security features of the same or a different type.

The pigments according to the invention are preferably employed in printing inks for security printing since they can be dispersed well in the conventional printing inks, and printing processes can be employed very variably for the production of security features.

However, the pigments according to the invention can also be incorporated directly with good success into the base materials for security products, for example into paper, paper-like substances, such as boards, cardboards and the like and/or plastics. A random distribution of the pigments is achieved here, which can be detected from their optical and/or functional properties in the end product.

As already described above, the combination of visible properties with functional properties (magnetisability, electrical conductivity) which may be present in the pigments according to the invention can particularly advantageously be employed in security applications. Preference is therefore given for security applications to the use of pigments according to the invention which have a flake-form substrate and are coloured, and in particular those which exhibit a colour flop when viewed from different angles in coatings. This property alone provides print images, coatings, etc., which comprise the pigments according to the invention with a colour design which is readily evident and cannot be copied using photocopiers.

In addition, the functional properties of the pigments can be used either to detect this property (for example electrical conductivity, magnetisability) qualitatively and/or quantitatively as such, or alternatively via coatings in the form of patterns, lines, logos, alphanumeric characters, etc., also to render the latter machine-readable through full or partial production by means of the pigments according to the invention. The authenticity of documents, for example, can thus be demonstrated if a print image, which is advantageously optically variable, i.e. has a colour flop when viewed under the action of natural or artificial light, contains an electrically conductive or magnetisable "fingerprint" which is only visible and/or detectable by machine, which provides the document with a further security element. It is sufficient here for the "fingerprint" merely to contain the print image of the individual pigments on a predetermined area, as arises by chance during printing. Random images of this type can be recorded technically by computers during manufacture of the products and called up again during later authenticity checking of these products. Coatings which comprise the pigments according to the invention can, in addition, be described or coded in the still-moist state using conventional fixed magnets, enabling both visible and also machine-readable security features to be produced.

It is of particular advantage that, given a suitable substrate and suitable layer thicknesses, the pigments according to the invention combine both the desirable optical (colour flop) and also the desirable functional properties. Particularly suitable for this purpose are the pigments according to the invention which have a substantially transparent, flake-form substrate, for example comprising mica, glass or $SiO_2$.

In the agricultural sector, the pigments can be used for colouring seed and other starting materials, in addition in the foods sector for the pigmentation of foods. The pigments according to the invention can likewise be employed for the pigmentation of coatings in medicaments, such as, for example, tablets or dragees.

All known thermoplastics, as described, for example, in Ullmann, Vol. 15, pp. 457 ff., Verlag VCH, and papers of all known types and compositions can be used for laser marking using the pigments according to the invention. Suitable plastics are, for example, polyethylene, polypropylene, polyamides, polyesters, polyester-esters, polyether-esters, polyphenylene ether, polyacetal, polybutylene terephthalate, polymethyl acrylate, polyvinyl acetate, polystyrene, acrylonitrile-butadiene-styrene, acrylonitrile-styrene-acrylate, polycarbonate, polyether sulfones, polyether ketones and copolymers and/or mixtures thereof.

The pigments according to the invention are incorporated into the thermoplastic by mixing the plastic granules with the interference pigment and then shaping the mixture under the action of heat. During incorporation of the interference pigments, adhesives, organic polymer-compatible solvents, stabilisers and/or surfactants which are temperature-stable under the working conditions, all of which are known to the person skilled in the art, can be added to the plastic granules. The pigmented plastic granules are generally produced by introducing the plastic granules into a suitable mixer, wetting the granules with any additives and then adding and mixing in the interference pigment. The mixture obtained in this way can then be processed directly in an extruder or injection-moulding machine. The marking is subsequently carried out using suitable radiation.

In the case of paper, the pigments can be incorporated into the coating and/or into the paper pulp.

During the marking, use is preferably made of high-energy radiation, generally in the wavelength range from 157 to 10,600 nm, in particular in the range from 300 to 10,600 nm. Mention may be made here by way of example of $CO_2$ lasers (10,600 nm), Nd:YAG lasers (1064 or 532 nm) or pulsed UV lasers (excimer lasers). The excimer lasers have the following wavelengths: $F_2$ excimer laser (157 nm), ArF excimer laser (193 nm), KrCl excimer laser (222 nm), KrF excimer laser (248 nm), XeCl excimer laser (308 nm), XeF excimer laser (351 nm), frequency-multiplied Nd:YAG lasers having wavelengths of 355 nm (frequency-tripled) or 265 nm (frequency-quadrupled). Particular preference is given to the use of Nd:YAG lasers (1064 or 532 nm) and $CO_2$ lasers. The energy densities of the lasers employed are generally in the range from 0.3 $mJ/cm^2$ to 50 $J/cm^2$, preferably 0.3 $mJ/cm^2$ to 10 $J/cm^2$.

The laser inscription is carried out by bringing the test specimen into the ray path of a pulsed laser, preferably a $CO_2$ or Nd:YAG laser. Furthermore, inscription using an excimer laser, for example via a mask technique, is possible. However, the desired results can also be achieved using other conventional types of laser which have a wavelength in a region of high absorption of the laser light-absorbent substance used. The marking obtained is determined by the irradiation time (or number of pulses in the case of pulsed lasers) and irradiation power of the laser and of the plastic system or coating system used. The power of the lasers used depends on the particular application and can readily be determined by the person skilled in the art in each individual case.

On use of pulsed lasers, the pulse frequency is generally in the range from 1 to 30 kHz. Corresponding lasers which can be employed in the process according to the invention are commercially available.

The pigments according to the invention can be used for laser marking in all above-mentioned plastics and in paper. The plastics pigmented in this way can be used as mouldings in the electrical, electronics and motor vehicle industries. A further important area of application for laser inscription is in documents of value of a very wide variety of types and plastic tags for the individual tagging of animals. The proportion of pigments in the plastic is 0.01 to 10% by weight, preferably 0.05 to 5% by weight and in particular 0.1 to 3% by weight in the case of laser marking in the applications. The labelling and inscription of casings, lines, key caps, ornamental strips and functional parts in the heating, ventilation and cooling sectors or switches, plugs, levers and handles which consist of the plastics pigmented with the pigments according to the invention can be carried out with the aid of laser light even in places which are difficult to access. The markings are distinguished by the fact that they are wipe- and scratch-resistant, are stable during subsequent sterilisation processes and can be applied in a hygienically clean manner during the marking process.

In the above-mentioned areas of application, the pigments according to the invention are likewise suitable for use in blends with all known organic or inorganic dyes and/or pigments. Organic pigments and dyes are, for example, monoazo pigments, disazo pigments, polycyclic pigments, cationic, anionic or nonionic dyes. Inorganic dyes and pigments are, for example, white pigments, coloured pigments, black pigments or effect pigments. Examples of suitable effect pigments are metal-effect pigments, pearlescent pigments or interference pigments, which are generally based on mono- or multicoated flakes based on mica, glass, $Al_2O_3$, $Fe_2O_3$, $SiO_2$, etc. Examples of structures and particular properties of the said pigments are given, for example, in RD 471001 or RD 472005, the disclosure content of which is hereby incorporated into the present invention by way of reference. In addition, further colorants which are suitable for blending with the pigments according to the invention are luminescent dyes and/or pigments and holographic pigments or LCPs (liquid crystal polymers). The pigments according to the invention can be mixed in any ratio with commercially available pigments and fillers.

If the pigments have a dark mass tone, they can also be employed in various formulations instead of carbon black for the production of hiding power.

Fillers which may be mentioned are, for example, natural and synthetic mica, nylon powder, pure or filled melamine resins, talc, glasses, kaolin, oxides or hydroxides of aluminium, magnesium, calcium, zinc, BiOCl, barium sulfate, calcium sulfate, calcium carbonate, magnesium carbonate, carbon, and physical or chemical combinations of these substances. There are no restrictions regarding the particle shape of the filler. It can be, for example, in flake form, spherical or needle-shaped in accordance with requirements.

The pigments according to the invention are furthermore suitable for the preparation of flowable pigment compositions and dry preparations comprising one or more particles according to the invention, binders and optionally one or more additives. Dry preparations are also taken to mean preparations which comprise 0 to 8% by weight, preferably 2 to 8% by weight, in particular 3 to 6% by weight, of water and/or a solvent or solvent mixture. The dry preparations are preferably in the form of pellets, granules, chips, sausages or briquettes and have particle sizes of 0.2-80 mm. The dry preparations are used, in particular, in the preparation of printing inks and in cosmetic formulations.

The complete disclosure content of all patent applications, patents and publications mentioned above is present in this application by way of reference.

The examples below are intended to explain the invention in greater detail, but without limiting it.

EXAMPLES

Example 1

100 g of mica having a particle size of 10-60 µm are heated to 75° C. with stirring in 1.9 l of demineralised water. The pH of the suspension is adjusted to 3.0 using 10% hydrochloric acid. 200 g of a 30% FeCl₃ solution are then metered in, during which the pH is kept constant by simultaneous dropwise addition of a 32% sodium hydroxide solution. The product is filtered off, washed, dried and reduced at 750° C. in a gas mixture comprising nitrogen and hydrogen (proportion of hydrogen: 8% by vol.), giving a lustrous pigment having silver interference, a grey-black mass tone and high lustre whose coating consists of 74% by weight of metallic iron.

Example 2

100 g of mica having a particle size of 10-60 μm are heated to 75° C. with stirring in 1.9 l of demineralised water. The pH of the suspension is adjusted to 3.0 using 10% hydrochloric acid. 300 g of a 30% FeCl₃ solution are then metered in, during which the pH is kept constant by simultaneous dropwise addition of a 32% sodium hydroxide solution. The product is filtered off, washed, dried and reduced at 600° C. in a gas mixture comprising nitrogen and hydrogen (proportion of hydrogen: 8% by vol.), giving a lustrous pigment having gold-coloured interference, a grey-black mass tone and high lustre whose coating consists of 26% by weight of metallic iron.

Example 3

The dried pigment from Example 2 is reduced at 800° C. in a gas mixture comprising nitrogen and hydrogen (proportion of hydrogen: 8% by vol.), giving a lustrous pigment having gold-coloured interference, a grey-black mass tone and high lustre whose coating consists of 80% by weight of metallic iron.

Example 4

100 g of SiO₂ flakes (thickness 365 nm) having a particle size of 10-60 μm are heated to 85° C. with stirring in 1.9 l of demineralised water. The pH of the suspension is adjusted to 2.8 using 10% hydrochloric acid. 1149 g of a 7% FeCl₃ solution are then metered in, during which the pH is kept constant by simultaneous dropwise addition of a 32% sodium hydroxide solution. The product is filtered off, washed, dried and reduced at 700° C. in a gas mixture comprising nitrogen and hydrogen (proportion of hydrogen: 8% by vol.), giving a lustrous, opaque pigment having a colour flop proceeding from red to gold and high lustre whose coating consists of 44.5% by weight of metallic iron.

Comparative Example

Corresponding to EP 0246523

100 g of mica having a particle size of 10-60 μm are heated to 80° C. with stirring in 2.5 l of demineralised water. The pH of the suspension is adjusted to 8.0 using 15% sodium hydroxide solution. A solution consisting of 600 g of FeSO₄*7 H₂O, 50 ml of concentrated sulfuric acid and 2000 ml of water and simultaneously a second solution consisting of 150 g of KNO₃ and 2000 ml of water is then metered in over the course of one hour, during which the pH is kept constant by addition of 15% sodium hydroxide solution. The product is filtered off, washed and dried at 100° C. for 3 hours, giving a non-lustrous, matt, black pigment whose coating consists of 100% by weight of magnetite.

Laser Marking:

PP granules (PP-HD, Stamylan PPH 10 from DSM) are processed by injection moulding by addition of 0.1% by weight of the pigment from Example 1. The moulding obtained (platelet) is subsequently inscribed using an SHT-Nd:YAG laser. At a pulse frequency of 2.5 kHz and a writing speed of 300 mm/s, the platelets exhibit a black, high-contrast and abrasion-resistant inscription. With increasing energy density, the inscription becomes increasingly darker.

The invention claimed is:

1. A pigment comprising
   a substrate comprising a titanium oxide, synthetic mica, natural mica, a phyllosilicate, glass, SiO₂, Al₂O₃, graphite, and/or BiOCl, and
   on the substrate an iron-containing coating consisting of FeO and/or Fe₃O₄ and metallic iron, wherein the metallic iron is present in an amount of 60-85% by weight of the iron-containing coating, and wherein said iron-containing coating has a thickness of 1-300 nm,
   wherein the resultant pigment is magnetisable and/or electrically conductive and exhibits interference effects.

2. The pigment according to claim 1, obtained by reaction of the substrate which has an iron oxide-containing coating as the outermost layer and is optionally additionally coated with one or more layers, in a reducing gas mixture comprising nitrogen and hydrogen with formation of metallic iron, and optionally further coating with one or more further layers.

3. The pigment according to claim 1, having a proportion of metallic iron in the iron-containing coating of 74% by weight, based on the iron-containing coating.

4. The pigment according to claim 1, wherein the substrate is in flake form.

5. The pigment according to claim 1, wherein one or more layers comprising one or more metal oxides, metal oxide hydrates, metal suboxides, metals, metal fluorides, metal nitrides, metal oxynitrides and/or mixtures thereof are additionally present between the coating comprising metallic iron and the substrate.

6. The pigment according to claim 1, wherein one or more layers comprising one or more metal oxides, metal oxide hydrates, metal suboxides, metal fluorides, metal nitrides, metal oxynitrides and/or mixtures thereof are additionally present on the coating comprising metallic iron.

7. The pigment according to claim 1, further comprising an additional inorganic and/or organic coating as the outer layer.

8. A seed, food, laser-markable material or pharmaceutical coating, comprising a pigment according to claim 1.

9. A process for the preparation of the pigment according to claim 1, comprising reacting a substrate which has an iron oxide-containing coating as the outermost layer and is optionally additionally coated with one or more layers in a reducing gas mixture comprising nitrogen and hydrogen with formation of metallic iron and optionally coating with one or more further layers.

10. The process according to claim 9, having a proportion of hydrogen in the gas mixture comprising nitrogen and hydrogen of 2.5 to 25% by volume.

11. The process according to claim 9, wherein reducing is carried out at temperatures of 400 to 1000° C.

12. The process according to claim 9, wherein an inorganic and/or organic coating is additionally applied as the outer layer.

13. A method of preparing a product selected from the group consisting of cosmetics, surface coatings, inks, plastics, films, security applications, seed colouring, food colouring, laser marking and pharmaceutical coatings, comprising incorporating the pigment of claim 1 in said product.

14. The method according to claim 13, wherein said pigments are present in a blend with one or more organic or inorganic dyes and/or pigments.

15. A product selected from the group consisting of security application, documents of value, banknotes, cheques, credit cards, shares, passports, identity documents, access authorisation identity cards, driving licences, entry tickets, revenue stamps, postage stamps, labels, seals, packaging materials, packaging of pharmaceuticals, foods, perfumes, cigarettes, clothing, shoes, household articles, and domestic electronic articles, said product having at least one security feature which comprises the pigment according to claim 1.

16. The product according to claim 15, wherein the security feature is a printed security feature which is printed by a printing ink comprising at least one of said pigment.

17. The product according to claim 15, wherein the security feature comprises said pigment incorporated directly into the base material for paper, board, cardboard and/or plastics and randomly distributed therein and in the end product produced therefrom.

18. The product according to claim 15, wherein the security feature is machine-readable.

19. The product according to claim 15 which includes at least one further security feature of the same or a different type.

\* \* \* \* \*